US00PP34641P3

(12) United States Plant Patent
Post

(10) Patent No.: US PP34,641 P3
(45) Date of Patent: Oct. 11, 2022

(54) ***CHRYSANTHEMUM* PLANT NAMED 'DLFALMA3'**

(50) Latin Name: ***Chrysanthemum* X *morifolium***
Varietal Denomination: 'DLFALMA3'

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/502,476

(22) Filed: Oct. 15, 2021

(65) Prior Publication Data

US 2022/0124951 P1 Apr. 21, 2022

Related U.S. Application Data

(60) Provisional application No. 63/093,198, filed on Oct. 17, 2020.

(51) Int. Cl.
*A01H 5/02* (2018.01)
*A01H 6/14* (2018.01)

(52) U.S. Cl.
USPC ..... Plt./286
CPC ..... *A01H 6/1424* (2018.05)

(58) Field of Classification Search
USPC ..... Plt./286, 297
CPC ..... A01H 5/02; A01H 5/0255; A01H 5/08; A01H 6/14; A01H 6/1424; A01H 6/7445; A01H 5/00
See application file for complete search history.

(56) References Cited

PUBLICATIONS

Cabi 2022 Fusarium oxysporum f.sp. chrysanthemi, retrieved on Jan. 10, 2022, retrieved from the Internet at https://www.cabi.org/isc/datasheet/24626, 5 pp. (Year: 2022).*
Deliflor Chrysanten Delishow 2019, retrieved on Jan. 6, 2022, retrieved from the Internet at https://www.deliflor.nl/15579/Delishow-2019, 2 pp. (Year: 2019).*
Upov Pluto 20220104, retrieved on Jan. 6, 2022, retrieved from the Internet at https://pluto.upov.int/result, one page. (Year: 2022).*

* cited by examiner

*Primary Examiner* — June Hwu
(74) *Attorney, Agent, or Firm* — C. Anne Whealy

(57) ABSTRACT

A new and distinct cultivar of *Chrysanthemum* plant named 'DLFALMA3', characterized by its upright plant habit; uniform growth habit; dark green-colored leaves; uniform and freely flowering habit; strong upright flowering stems; single-type inflorescences with pale purple-colored ray florets; resistance to *Fusarium*; relative tolerance to low production temperatures; and good postproduction longevity.

1 Drawing Sheet

Figure 1:
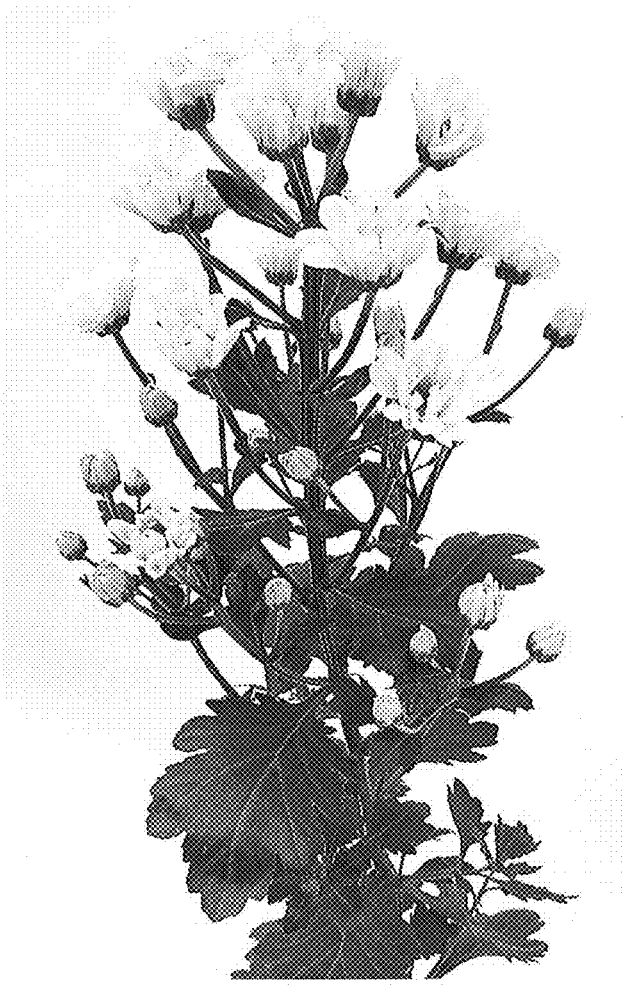

Botanical designation: *Chrysanthemum* X *morifolium*.
Cultivar denomination: 'DLFALMA3'.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on Aug. 2, 2020, application number A202700. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFALMA3'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant is a naturally-occurring whole plant mutation of *Chrysanthemum* x *morifolium* 'DLFALMA1', not patented. The new *Chrysanthemum* plant was discovered and selected as a single flowering plant from within a population of plants of 'DLFALMA1' in a controlled greenhouse environment in Maasdijk, The Netherlands in November, 2018.

Asexual reproduction of the new *Chrysanthemum* plant by vegetative terminal cuttings since November, 2018 in a controlled greenhouse environment in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFALMA3'. These characteristics in combination distinguish 'DLFALMA3' as a new and distinct *Chrysanthemum* plant:

1. Upright plant habit; uniform growth habit.
2. Dark green-colored leaves.
3. Uniform and freely flowering habit.
4. Strong upright flowering stems.
5. Single-type inflorescences with pale purple-colored ray florets.
6. Resistant to *Fusarium* (*Fusarium oxysporum*).
7. Relatively tolerant to low production temperatures.
8. Good postproduction longevity.

Plants of the new *Chrysanthemum* differ primarily from plants of the mutation parent, 'DLFALMA1' in ray floret color as ray florets of plants of the new *Chrysanthemum* are pale purple in color whereas ray florets of plants of 'DLFALMA1' are white in color.

Plants of the new *Chrysanthemum* can be compared to plants of *Chrysanthemum* X *morifolium* 'DLFETO3', not patented. In side-by-side comparisons, plants of the new *Chrysanthemum* differ primarily from plants of 'DLFETO3' in ray floret color as ray florets of plants of the new *Chrysanthemum* are lighter purple in color than ray florets of plants of 'DLFETO3'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph at the top of the sheet (FIG. 1) comprises a side perspective view of a typical flowering stem of 'DLFALMA3' grown as a spray-type cut flower.

Figure 2:
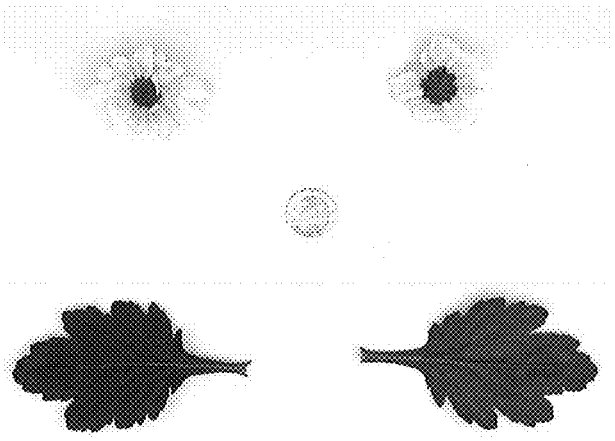

The photograph at the bottom of the sheet (FIG. 2) is a close-up view of upper (left) and lower (right) surfaces of typical inflorescences (top of figure) and typical leaves (bottom of figure) of 'DLFALMA3'.

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFALMA3'.

Parentage: Naturally-occurring whole plant mutation of *Chrysanthemum* x *morifolium* 'DLFALMA1', not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous single-type cut flower that is typically grown as a single stem spray-type; upright plant habit; vigorous growth habit and rapid growth rate.

*Plant height, soil level to top of foliar plane*.—About 60 cm.

*Plant height, soil level to top of inflorescence plane*.—About 66.4 cm.

*Plant (spray) diameter*.—About 20.7 cm.

*Flowering stem length*.—About 58.7 cm.

*Flowering stem diameter*.—About 7 mm.

*Flowering stem internode length*.—About 2.3 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 143B.

*Flowering stem color, developed*.—Close to 146A.

*Leaf description*.—Arrangement: Alternate; simple. Length: About 10.7 cm. Width: About 7 cm. Shape, in overall outline: Broadly ovate. Apex: Abruptly acute, minute. Base: Attenuate. Margin: Palmately lobed, coarsely dentate to serrate; sinuses convergent to parallel and shallow to medium in depth. Texture and luster, upper surface: Moderately to densely pubescent, not rugose; moderately velvety; slightly glossy. Texture and luster, lower surface: Moderately to densely pubescent, prominent venation; slightly velvety; slightly glossy. Venation pattern: Pinnate, reticulate. Color: Developing leaves, upper surface: Close to NN137A. Developing leaves, lower surface: Close to between 138A and 147B. Fully developed leaves, upper surface: Close to between NN137A and 147A; venation, close to 147B. Fully developed leaves, lower surface: Close to 147B; venation, close to 146B. Petioles: Length: About 7 mm. Diameter: About 3 mm by 4 mm. Strength: Moderately strong. Texture and luster, upper and lower surfaces: Moderately pubescent; slightly glossy. Color, upper surface: Close to 146B to 146C; edges, close to NN137B. Color, lower surface: Close to 147B; edges, close to 137B. Stipules: Quantity and appearance: Two leafy stipules, opposite, at the petiole attachment to the stem. Length: About 6 mm. Width: About 4 mm. Shape, in overall outline: Roughly ovate. Texture and luster, upper and lower surfaces: Moderately densely pubescent; slightly glossy. Color, upper surface: Close to between NN137A and 147A. Color, lower surface: Close to 147B.

Inflorescence description:

*Appearance*.—Single-type inflorescence form with obovate to elliptic-shaped ray florets and tubular disc florets; inflorescences borne perpendicular to peduncles and face upright to about 25° from vertical; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 50 days later when grown as a spray-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a spray-type, about 31 inflorescences develop per flowering stem.

*Inflorescence size*.—Diameter, grown as a spray-type: About 6.8 cm. Depth (height), grown as a spray-type: About 3 cm. Disc diameter, grown as a spray-type: About 1.4 cm.

*Receptacles*.—Height: About 3 mm. Diameter: About 7 mm. Shape: Flattened globular. Color: Close to 145A and 145C.

*Inflorescence buds*.—Height: About 1.7 cm. Diameter: About 1.4 cm. Shape: Ovoid. Texture and luster: Moderately pubescent; slightly glossy. Color: Developing involucral bracts, close to NN137B and 138A; developing ray florets, close to 75C.

*Ray florets*.—Quantity and arrangement: About 26 arranged in about two whorls. Length: About 3.6 cm, varying between 3.4 cm and 3.8 cm. Width: About 1.4 cm, varying between 1.3 cm and 1.5 mm. Shape: Obovate to elliptic; slightly convex, moderately carinate and slightly twisting. Apex: Shallowly praemorse. Base: Cuneate and fused at the base. Margin: Entire; not undulate. Aspect: About 10° to 25° from vertical. Texture and luster, upper surface: Smooth, glabrous; moderately velvety; matte. Texture and luster, lower surface: Smooth, glabrous; slightly velvety; slightly glossy. Color: When opening, upper surface: Close to between 75D and 76D. When opening, lower surface: Close to between 76D and N155B. Fully opened, upper surface: Close to between N155B and NN155D; venation, close to between N155B and NN155D; color does not change with subsequent development. Fully opened, lower surface: Close to N155B; venation, close to N155B; color does not change with subsequent development.

*Disc florets*.—Quantity and arrangement: About 130 at the center of the receptacle. Length: About 5 mm. Diameter: About 1 mm. Shape: Lower 80% fused into a tube; upper 20% free. Apex: Acute. Margin, free-part: Entire. Texture and luster, inner and outer surfaces: Smooth, glabrous; glossy. Color, when opening, inner and outer surfaces: Close to 157B; proximally, close to 145D and at the apex, close to 2B. Color, fully opening, inner and outer surfaces: Close to 157B; proximally, close to 145D and at the apex, close to 2B.

*Involucral bracts*.—Quantity and arrangement: About 18 arranged in about two whorls. Length: About 8 mm. Width: About 5.5 mm. Shape: Broadly ovate. Apex: Obtuse. Base: Cuneate. Margin: Entire. Texture and luster, upper surface: Smooth, glabrous; glossy. Texture and luster, lower surface: Moderately pubescent; matte. Color, upper surface: Close to 146A; lateral margins, translucent and close to 145C to 145D and apical margins tinged with close to N199A. Color, lower surface: Close to NN137A; lateral margins, translucent and close to 145C to 145D and apical margins tinged with close to N199A.

*Peduncles*.—Length, terminal peduncle: About 3.9 cm. Diameter, terminal peduncle: About 2.5 mm. Length, third peduncle: About 6.2 cm. Diameter, third peduncle: About 3 mm. Strength: Strong. Aspect, terminal peduncle: Upright. Aspect, third peduncle: About 45° from the flowering stem axis. Texture and luster: Moderately pubescent; moderately glossy. Color: Close to 137A.

*Reproductive organs*.—Androecium: Present on disc florets only. Quantity: About five per floret. Filament length: About 2 mm. Filament color: Close to 145D. Anther size: About 0.5 mm by 1.5 mm. Anther shape: Oblong. Anther color: Close to 151B. Pollen amount: Scarce. Pollen color: Close to 14A. Gynoecium: Present on both ray and disc florets. Quantity: One per floret. Pistil length: About 5 mm. Style length: About 4.5 mm. Style color: Close to 145A. Stigma diameter: About 1 mm. Stigma shape: Cleft to three-parted, decurrent. Stigma color: Close to 151D. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* Wilt (*Fusarium oxysporum* f. sp. *chrysanthemi* (strain FoNL1)). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFALMA3' as illustrated and described.

* * * * *